United States Patent
Loriga et al.

(10) Patent No.: US 7,869,866 B2
(45) Date of Patent: Jan. 11, 2011

(54) DEVICE FOR THE MONITORING OF PHYSIOLOGIC VARIABLES THROUGH MEASUREMENT OF BODY ELECTRICAL IMPEDANCE

(75) Inventors: Giannicola Loriga, Monasterace (IT); Andrea Scozzari, Leghorn (IT)

(73) Assignee: Smartex S.r.l., Prato (IT)

( * ) Notice: Subject to any disclaimer, the term of this patent is extended or adjusted under 35 U.S.C. 154(b) by 526 days.

(21) Appl. No.: 11/574,628

(22) PCT Filed: Sep. 6, 2005

(86) PCT No.: PCT/EP2005/054393

§ 371 (c)(1),
(2), (4) Date: Mar. 2, 2007

(87) PCT Pub. No.: WO2006/027360

PCT Pub. Date: Mar. 16, 2006

(65) Prior Publication Data

US 2008/0275361 A1    Nov. 6, 2008

(30) Foreign Application Priority Data

Sep. 6, 2004  (IT)  .................. PI2004A000060

(51) Int. Cl.
*A61B 5/00*    (2006.01)

(52) U.S. Cl. ...................................... 600/547; 600/300

(58) Field of Classification Search ................. 600/300, 600/547
See application file for complete search history.

(56) References Cited

U.S. PATENT DOCUMENTS

| | | | |
|---|---|---|---|
| 3,802,419 A | 4/1974 | Yates | |
| 3,882,851 A | 5/1975 | Sigworth | |
| 4,016,868 A * | 4/1977 | Allison | ........................ 600/388 |
| 5,588,429 A | 12/1996 | Isaacson | |
| 5,944,022 A * | 8/1999 | Nardella et al. | .............. 128/899 |
| 6,236,951 B1 | 5/2001 | Payne | |
| 6,377,845 B1 | 4/2002 | Kinast | |
| 6,631,292 B1 * | 10/2003 | Liedtke | ........................ 600/547 |
| 2004/0263376 A1 * | 12/2004 | Shimizu et al. | .............. 341/172 |

OTHER PUBLICATIONS

International Search Report for PCT/EP2005/054393, dated Dec. 1, 2005.
International Preliminary Report on Patentability for PCT/EP2005/054393, dated Dec. 19, 2006.

* cited by examiner

*Primary Examiner*—Max Hindenburg
*Assistant Examiner*—Renee Danega
(74) *Attorney, Agent, or Firm*—Abelman, Frayne & Schwab

(57) ABSTRACT

A device for the measurement of body impedance includes a current injecting device for injecting a test current through a first set of electrodes to the body of a patient, and a voltage reading device for reading voltage variations between two electrodes belonging to a second set of electrodes using a coherent demodulator.

32 Claims, 4 Drawing Sheets

DEVICE FOR THE MONITORING OF PHYSIOLOGIC VARIABLES THROUGH MEASUREMENT OF BODY ELECTRICAL IMPEDANCE

CROSS-REFERENCE TO RELATED APPLICATIONS

This application is a 371 of international application number PCT/EP2005/054393, filed on Sep. 6, 2005.

FIELD OF INVENTION

The present invention regards the field of monitoring of vital signals, and in particular the wearable systems for non invasive monitoring

BACKGROUND OF THE INVENTION

Impedance measurement is a technique presented in literature and already well studied since the sixties. In this document references will be done to patents that deal with similar problems, and then the differences between the present invention and those patents will be highlighted to clarify improvement and adaptation needed to the specific aspects of the current application.

The impedance measurement consists in evaluating the variation of body impedance after injecting an high frequency and low intensity current through two electrodes and measuring the voltage drop caused by such current. Measured impedance depends on the body composition and the flows of fluids across the body itself. Hence the different applications based on this technique: in nutrition science for calculating the body mass index, in cardiology (impedance cardiography) to monitor the cardiac output, in pneumology to check breathing, etc.

The Impedance Pneumography allows to monitor the respiratory activity relying on the thorax impedance variations determined by the air flow through lungs. An Impedancemetry system that uses only two electrodes shows acceptable results only with subjects in rest conditions. In order to improve the performance of the system, it is necessary to use a four wire measurement method, thus making use of four electrodes; the outer ones are exclusively used to inject a high frequency and low intensity current, while the inner ones allow the measurement of voltage variations due to the impedance changes caused by the respiratory activity.

The four electrodes measurement method, thanks to the high input impedance of the measurement amplifier, allows to remove the contribution of the resistance of the cable wire and the contact resistance between the electrodes and the skin, which could significantly alter the impedance we are trying to measure. Furthermore, the use of two electrodes to inject current, which are different from those used to measure the voltage, lets the spatial distribution of the current density between the measuring electrodes be approximately constant.

This allows to reduce the effect of impedance variations in proximity of the "injection" electrodes due to the higher current density in their proximity. Since measured impedance is function of the air volume present in lungs, such method can be calibrated with a spirometer.

The relationship between impedance change ($\Delta Z$) and air volume change ($\Delta V$) is approximately linear under most circumstances.

Coefficient $\Delta Z/\Delta V$ depends on physical dimensions of the subject and on the positioning of electrodes and is comprised between 0.3 and 1 ohm/liter. Hence the impedance variation corresponding to each respiratory cycle is inferior to 1% of the basic impedance.

In U.S. Pat. No. 3,802,419 in order to measure the voltage determined by the passage of high frequency current injected through a couple of surface electrodes, a standard full wave diode rectifier is used.

U.S. Pat. No. 3,882,851 indicates the use of a synchronous demodulator in the block diagram, the output signal of which is used to control the amplitude of the stimulating current. This is used to guarantee that the variations of the measured voltage lie within an acceptable range, in order to compensate the drifts from which such a solution suffers.

SUMMARY OF THE INVENTION

The aim of this invention is to provide an idea for a simple, portable and easy-to-carry device, able to obtain precise measurements of the body impedance value. The solution proposed comprises an analog front-end measuring the impedance through a four-electrode methodology, with appropriate characteristics for the specific application, although usable also in other fields like nutrition science, cardiology, pneumology, etc.

It is a further aim of this invention to provide a device suitable for being implemented and integrated into wearable measurement systems, that is a device with a high immunity to several disturbance sources (of electromagnetic, mechanical and thermal kind), which are typical in a subject in motion, a device of small size and low power consumption in order to be easily integrated into said wearable measurement systems.

About the use of an apparatus of this type with the appropriate excitation frequencies, the state of the art literature indicates that the resistive contribution to the total impedance (real part) is predominant, and that, under such conditions, the required information can be obtained directly from the amplitude of the impedance measurement rather than from a vectorial measure; furthermore, the need to observe small percentage variations compared to the base value implies very strict requirements in terms of repeatability for the whole measurement chain.

The main functional blocks are constituted by a low distortion oscillator with an amplitude control based on a bandgap reference, a high-precision demodulator and the necessary gain stages. The sinusoidal current generator has to provide a low distortion oscillation (better of the 0.1%) and has to be stable in amplitude. The block of demodulation, called hereinafter "coherent demodulator", permits to obtain a measure of adequate precision at the required frequencies and in the foreseen environmental conditions (including the effects of movement).

For this reason a average detector, based on a coherent demodulator, has been preferred to a standard active diode rectifier, as the latter introduces disadvantages that do not match with the aforesaid precision requirements: commutation time (polarization and depolarization of the rectifier diodes) depends mostly from the open loop band of the OPAMP utilized, because in the transition phase diodes placed in the feedback chain are non conducting; also employing fast OPAMP, time that the system spends in order to adapt its output to the change of sign of the input signal can be a consistent fraction of the half-period (at the frequencies of interest, which are in the range 20 KHz÷100 KHz), introducing a measurement error on the demodulated signal that is not neglectable.

Moreover, such time depends heavily on the amplitude of the signal itself and on the ambient temperature, and can also show large variations among different samples of the same device. There are also practical problems due to the fact that the fast OPAMPs easily tend to oscillate when passing from non-linear to strong feedback conditions, and, on the other side, slow OPAMPs have a negative impact on the commutation delay problem, introducing the aforesaid error.

The demodulator used in this invention can be summarized in the following functional blocks: a differential amplifier with two outputs having opposite phase (one is inverted), a comparator, an SPDT switch and a low-pass filter; the entire chain described forms a high precision average detector.

Such demodulator, operating a phase shift of the output signal depending on the sign of the input signal, implies a relationship between the temporal error on the determination of the zero crossing point and the amplitude of the detected signal; for the calculation of such an effect and a quantification of the maximum acceptable error, as explained in the detailed description of the present invention. With the electronic components shown in the proposed schematic, the calculated error does not exceed 0.2% of the measured value.

A system structured in this fashion, therefore, allows to obtain satisfactory results in applications like the continuous monitoring of the respiratory activity (impedance pneumography) of a subject in motion, both using standard ECG Ag/AgCl and non-conventional fabric electrodes as a part of a wearable system, assuring a high robustness to movement artifacts, as demonstrated by tests performed on the prototypes.

DETAILED DESCRIPTION OF THE INVENTION

An impedance measurement system, due to the exiguous body impedance variations we intend to monitor, needs a demodulation system that guarantees precision of measurement, in the sense of the repeatability of measurement within ranges of tens of seconds, and possibly of minutes (i.e. a few respiratory periods); this implies tight requirements for the analog front-end and, specifically, for the average detector.

A preferred embodiment of the present invention, using a "coherent demodulation technique", allows to carry out a reliable measurement in electrically noisy situations and with fast temperature variations, conditions that permit its use also in wearable devices worn by subjects in motion.

Figure 1:
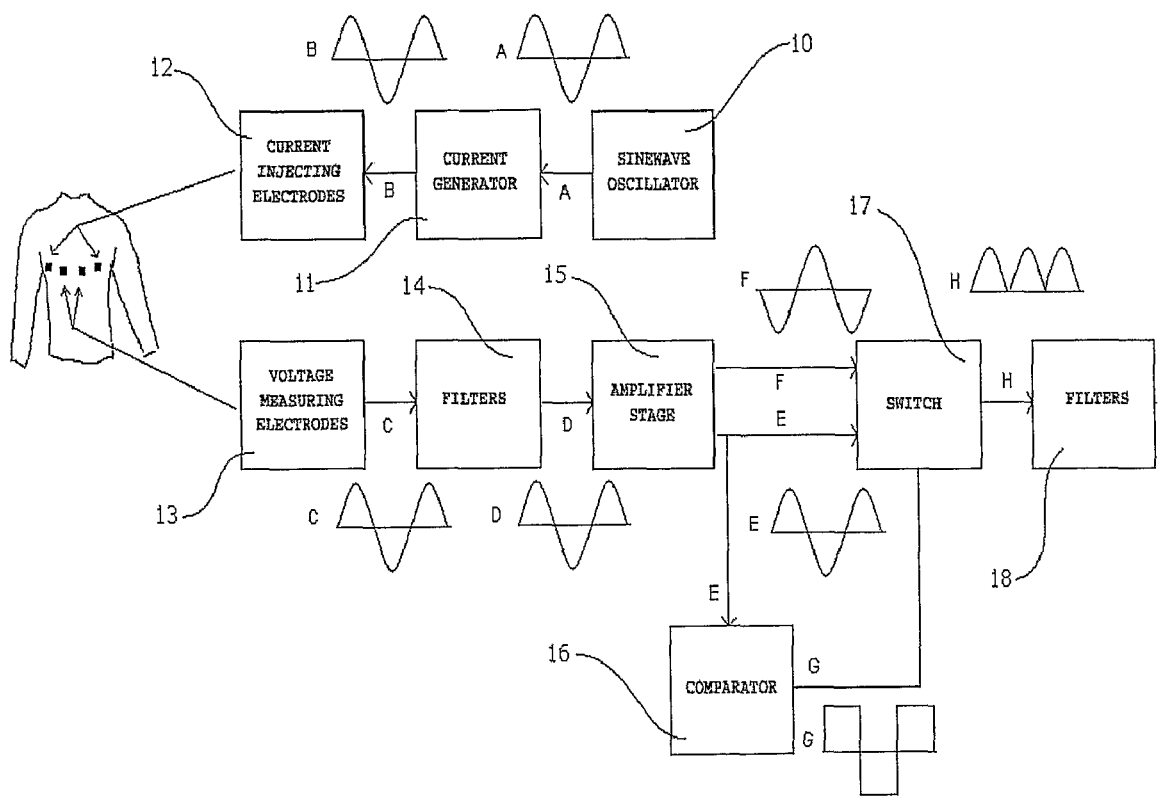
FIG. 1 shows a block diagram with the device functional blocks and includes a graphic description of the kind of treatment that each input sinewave undergoes through the measuring chain.

With reference to FIG. 1, said preferred embodiment of the present invention is depicted. A low distortion oscillator with amplitude control capability 10 delivers an amplitude stabilized sinewave at its output. Said sinewave is fed to a voltage-current converter 11 in order to obtain a high frequency, low intensity, sinusoidal current to be injected to the patient's body through the injection electrodes 12.

Then, a pair of receiving electrodes 13 measure the voltage drop of the body impedance between said two electrodes caused by said injected current. A filter 14 cleans the measured signal and then a differential amplifier 15 provides amplification to its input signal delivering two signals at its outputs, one in phase and the other opposite in phase with respect to the input signal. The output signal of the differential amplifier 15 which is in phase with respect to its input signal, is fed to a fast comparator 16, the output of which, a square wave, is fed to the control input of a fast switch 17 together with said two outputs of said differential amplifier 15. The square wave acts as the control signal for said fast switch 17 that is driven to deliver at its output a rectified sinewave.

Said comparator 16 and said switch 17 together form a coherent demodulator, the output of which—said rectified sinewave—is finally fed to a low pass filter 18 that extracts the average value of said output of the coherent demodulator.

In a further preferred embodiment of the present invention, the output of said low distortion oscillator with amplitude control capability 10 is fed to said fast comparator 16 instead of the output signal of the differential amplifier 15 which is in phase with respect to its input signal. With this topology, the output signal of said low pass filter 18 will be proportional to the real part of the impedance that is measured.

In a further preferred embodiment of the present invention, the two cold terminal electrodes of each one of said set of electrodes are electrically connected together and in a further preferred embodiment of the present invention, both the hot and the cold terminal electrodes of each one of said set of electrodes are electrically connected together. These topologies allow an easier measurement to be carried on even if the signal that is read requires a higher degree of filtering due to the higher amount of electromagnetic interference that is picked up.

In applications like the use of the thoracic impedance for monitoring the breathing activity, the frequency of said sinewave can vary between 20 kHz and 100 kHz with a peak amplitude of a few mA. Currents with such characteristics have too high frequency and too low amplitude to stimulate the biological tissue. An aspect of fundamental importance is to obtain an oscillation with distortion inferior to the 0.1%.

If the chosen oscillation frequency is 50 kHz, a sinusoid with requested requirements can be obtained through a classical Wien's bridge configuration. As an alternative, an appropriate digitally programmable frequency synthesizer can be used.

Advantageously, in a preferred embodiment of the present invention, said oscillator 10 comprises an additional feedback loop for the stabilization of the output signal amplitude, having a "large" time constant with respect to the period of the generated signal; this feature being very effective to compensate variations caused by temperature changes (i.e., from inside to outside passages) or by the power supply.

Preferably, we will use the oscillator output, extracting the peak value and comparing such value with an appropriate voltage reference having high stability, e.g. of the bandgap effect type. Preferably, the difference between these two values can be measured through a differential amplifier, e.g., as a possible solution, a AD620 of Analog Devices could be used. AD620 output could be used to control an OTA (transconductance OPAMP), e.g. the CA3080 of INTERSIL, with the purpose to stabilize the voltage to the wished value.

Figure 2:
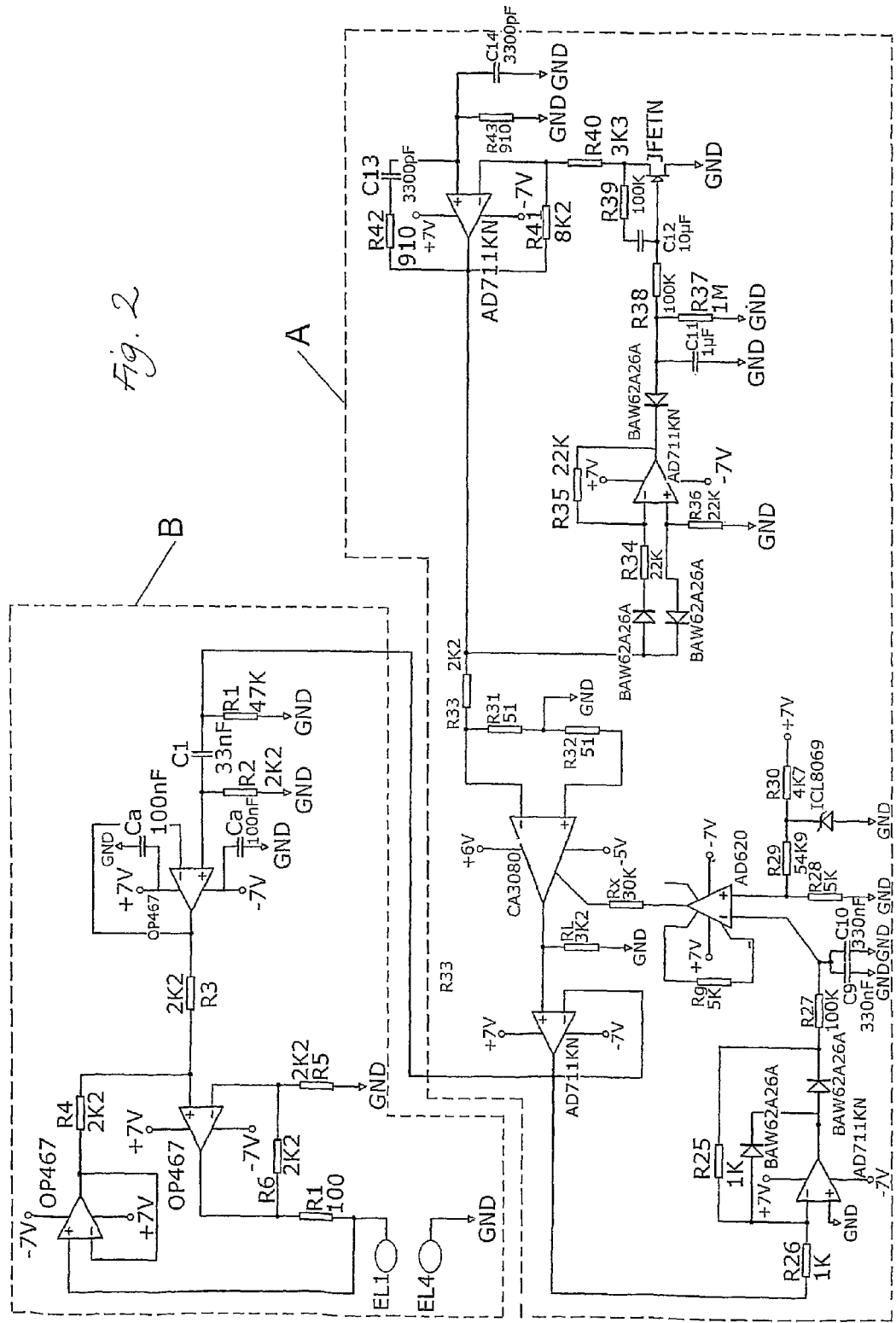
FIG. 2 shows an electrical schematic of a preferred embodiment of the oscillating block (including the stabilizing system) and of the voltage-to-current converter.

FIG. 2 shows a further preferred embodiment of the present invention to obtain one sinewave at 50 kHz and 300 mV of peak amplitude. The successive stage is a voltage-to-current converter that allows to obtain the already cited current at 50 kHz and 3 mA of peak amplitude; this is formed by an analog adder and a buffer stage, in which the adder stage has, at its inputs, the control voltage and the one picked up at the lower terminal of the reference resistor $R_f$; the current imposed to the load is then equal to the ratio between the control voltage and $R_f$, till the open loop gain of the OPAMPs is large enough to make the virtual short circuit principle true.

Such a Solution, even if not binding, is preferred because has sufficient bandwidth to guarantee the necessary swing of the output signal at the frequency of interest. The use of the described device is not restricted to electrodes in textile material only, but is compatible and usable with whichever type of electrodes, wherever located. In the preferred disposition, which is not binding, the current is injected through the outer electrodes determining a voltage drop due to the skin impedance. Such voltage difference is detected by the pair of inner electrodes.

The value of the impedance changes depending on the presence of air in lungs, more precisely according to the modification of the internal volume due to the breathing activity. The voltage drop read from electrodes EL2 and EL3 is amplified through a differential amplifier able to work at the frequency of 50 kHz without introducing appreciable distortions in the measure.

A possible solution for the amplification block can be the classical instrumentation amplifier composed by using 3 OPAMPs. The high value of the differential input impedance allows to minimize the loading effect on the measurement system. The high value of the CMRR permits to reduce common-mode components.

Figure 3:
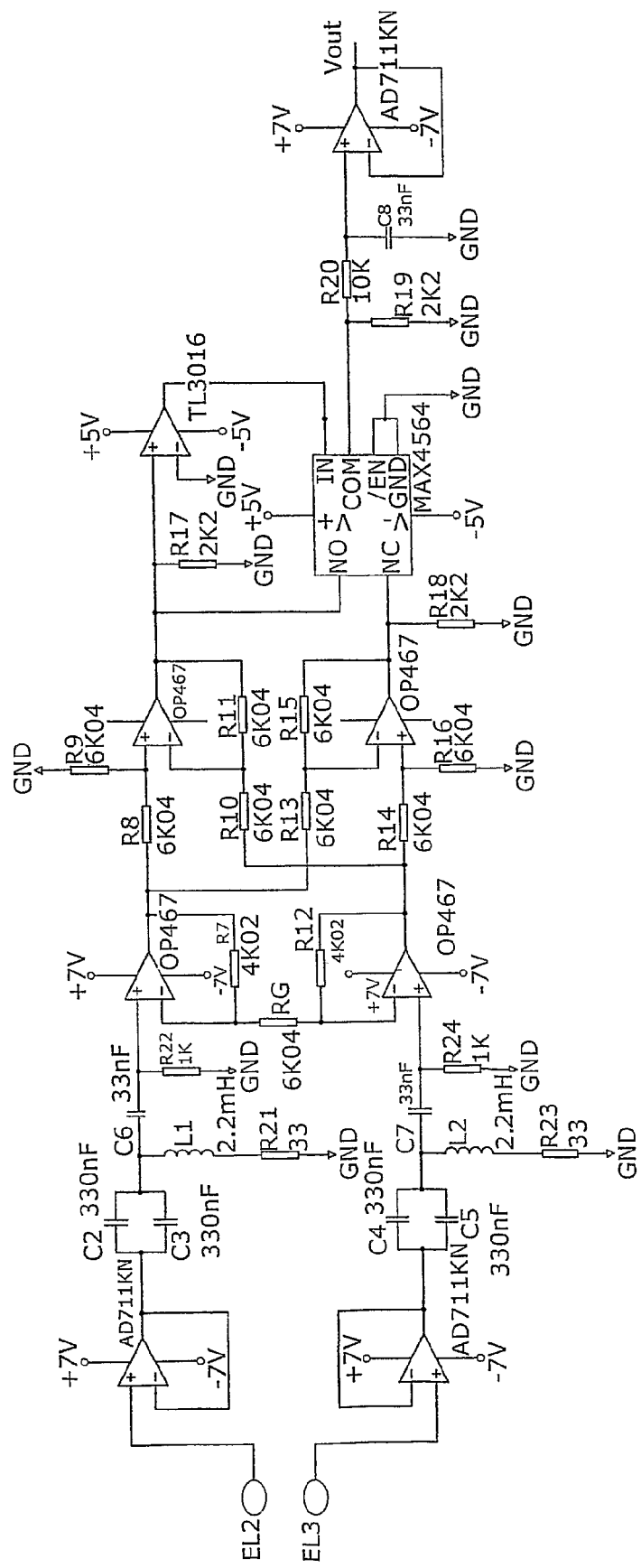
FIG. 3 shows an electrical schematic of the measurement chain including, among others, the filtering block, the differential amplifier block with two opposite in phase outputs and the coherent demodulator.

Preferably, another OPAMP will be added in order to obtain an inverted output, necessary for the successive block. OP467 of Analog Devices, which is shown in the schematic in FIG. 3, is an example of an operational amplifier able to provide the required performance at frequencies of the order of hundreds of kHz.

The following block, composed by the combination of a comparator and a fast switch (coherent demodulator) and followed by a low-pass filter, allows to obtain a detection of amplitude that respects the established requirements. The output signal from the average detector will be proportional to the impedance amplitude seen between electrodes EL2 and EL3.

The switch device has at its inputs the amplified signals, ideally perfectly "in phase" and in "counter phase", with regards to the potential difference measurable at the electrodes. The "in phase" signal is also fed to the input of a fast comparator.

At the output of the comparator a square-wave is obtained which is still synchronized with the received signal. The fast comparator output represents the control signals of the Switch, that preferably, but not necessarily, could be constituted by two electronic switches controlled by inverted logics levels.

Thanks to such control, at the output of the switch, every half period, the signal coming from "in-phase" and "counter-phase" gain chains, are alternatively presented. As a result, at the output of the switch the rectified signal will be obtained (FIG. 1). A possible practical solution can be implemented, but not necessarily, with a MAXIM4564 (switch), and a TL3016 (fast comparator).

Considering that the device is thought for the realization of a impedance pneumograph, we have to take into account that the variation of thoracic impedance during respiration is approximately 1% of the base impedance. Using as a possible solution a sinewave oscillator able to provide an oscillation at 50 kHz and 300 mV of amplitude, and a voltage-to-current converter able to inject a peak current of 3 mA again at 50 kHz, signal variation at the output of the demodulator block accompanying the respiratory activity is in the range of 10-12 mV.

To give some rough figures, with an oscillation at 50 kHz a half period corresponds to 10 microseconds; an error of 1% on the location of the instant of the zero crossing corresponds here to 100 ns. Hence the necessity of using fast comparator and switch in the measurement chain. The Switch MAXIM4564, which has been used in the preferred embodiment, presents a '$t_{on}$' equal to 60 ns and a '$t_{off}$' equal to 40 ns (worst case).

Figure 4:
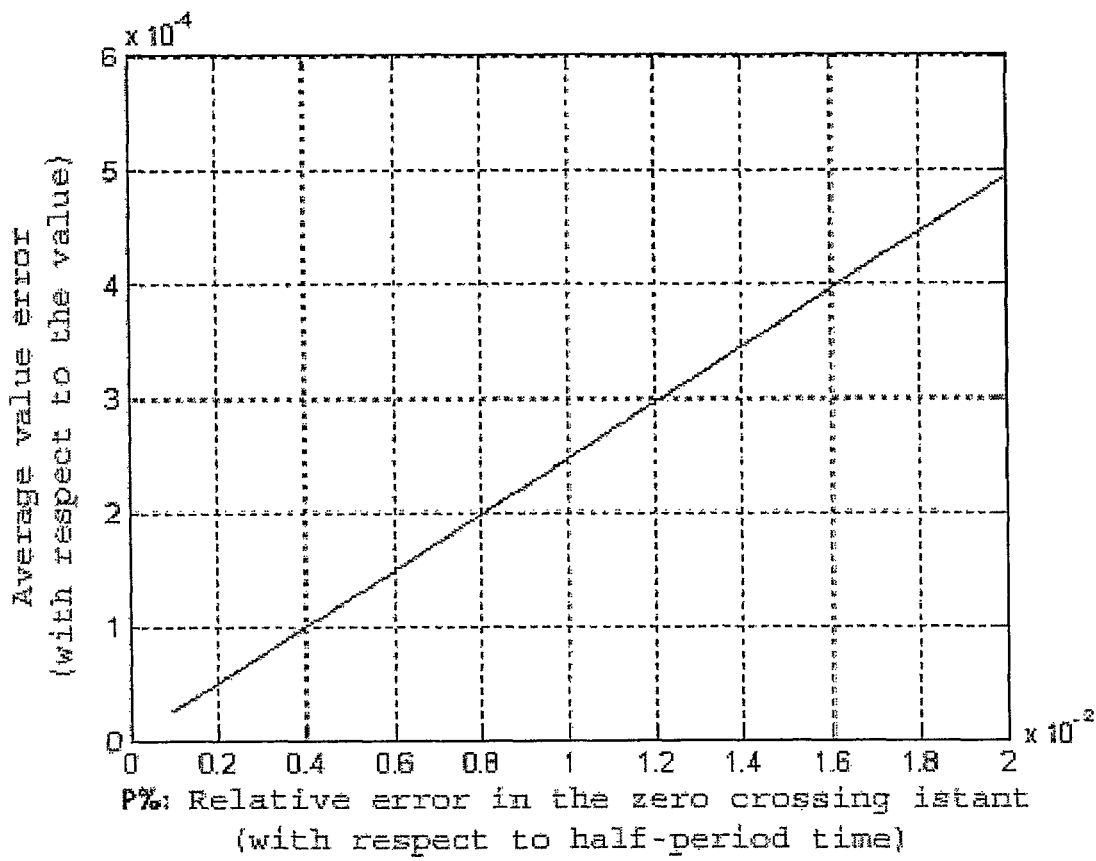
FIG. 4 shows the trend of the error on the average value of the rectified signal (percentage of the average value) versus the percentage error in the detection of the zero crossing instant.

Fast comparator TL3016 with a propagation delay of 7.6 ns allows to respect the imposed requirement. The mentioned components only constitutes a possible practical solution to the implementation and it is not binding to the patent purpose, that covers both the found solution and the schematic described in this document. In the proposed solution, the error in the rectified signal due to the error in the detection of the zero crossing instant lies in the range 0.1÷1%. FIG. 4 shows the effect of such error in the moment of sampling on the total error in the demodulation process.

P % indicates (in percentage terms) the ratio between the temporal error in the zero crossing and the half period duration; the error made in the extraction of the average value of the rectified signal versus P % is shown.

Such error has been calculated in terms of the relationship between the area subtended by the portion of sinewave not perfectly rectified (lack of change of sign due to error in the localization of the instant of zero crossing) and the area subtended by the sinewave in a half period.

In order to calculate the area subtended by the portion of not perfectly rectified sinewave, such sinewave was approximated with a Taylor development stopped at the $1^{st}$ order, calculated at the effective point of zero crossing. FIG. 4 shows that, in correspondence of a P % equal to 1%, the error in the signal demodulation is smaller of $3*10^{-4}$, to be interpreted as parts of the measured average value.

To obtain this demanding requirement, in this preferred embodiment, an amplitude detection system based on a coherent demodulator has been chosen, as this technology is easily available, while high specifications are hard to reach with classical full-wave diode demodulation systems, used in other impedance measurement devices described in the background of the invention.

The proposed exemplary embodiment introduces a wide dynamic and a high repeatability of the measure in the available dynamic range, which allows the easy realization of a measurement chain for continuous acquisition, which offers the possibility to observe the variations of the interesting signals in the above-mentioned conditions. This approach does not need drifts compensation systems, thanks to its high stability, while such compensation systems are instead required in the other examples listed in the Background of the invention.

Advantageously, the technique here proposed foresees an excitation signal with constant amplitude which guarantees an easy signal detection independently from environmental and installation conditions; moreover, it successfully manages situations without modifications of impedance in the short time, like in the case of the apnoeas.

The invention claimed is:

1. A device for the measurement of body impedance comprising: means for injecting a test current through a first set of electrodes to the patient's body, including: at least one oscillator and at least one voltage—current converter and means to read voltage variations between two electrodes belonging to a second set of electrodes including: a demodulator; at least one filter; at least one differential amplifier with two outputs having opposite phase and at least one low pass filter, wherein said at least one oscillator is a sinewave oscillator and wherein said demodulator is a coherent demodulator further including at least one comparator and at least one switch, and wherein the output of said sinewave oscillator is connected to the input of said voltage-current converter, the output of said voltage-current converter is connected to said first set of electrodes, said second set of electrodes is connected to the input of said at least one filter, the output of said at least one filter is connected to the input of said at least one differential amplifier, the first output of said at least one differential amplifier is connected to a first input of said at least one switch, the second output of said at least one differential amplifier is connected to a second input of said at least one switch and to the input of said at least one comparator, the output of said at least one comparator is connected to the control input of said at least one switch, the output of said at least one switch is connected to the input of said at least one low pass filter.

2. A device for the measurement of body impedance comprising: means for injecting a test current through a first set of electrodes to the patient's body, including: at least one oscillator and at least one voltage—current converter and means to read voltage variations between two electrodes belonging to a second set of electrodes including: a demodulator; at least one filter; at least one differential amplifier with two outputs having opposite phase and at least one low pass filter, wherein said at least one oscillator is a sinewave oscillator and wherein said demodulator is a coherent demodulator further including at least one comparator and at least one switch, and wherein the output of said sinewave oscillator is connected to the input of said voltage-current converter and to the input of said at least one comparator, the output of said voltage-current converter is connected to said first set of electrodes, said second set of electrodes is connected to the input of said at least one filter, the output of said at least one filter is connected to the input of said at least one differential amplifier, the first output of said at least one differential amplifier is connected to a first input of said at least one switch, the second output of said at least one differential amplifier is connected to a second input of said at least one switch, the output of said at least one comparator is connected to the control input of said at least one switch, the output of said at least one switch is connected to the input of said at least one low pass filter.

3. The device for the measurement of body impedance according to claim 1, wherein said first set and said second set of electrodes comprise two electrodes, one hot terminal and one cold terminal.

4. The device for the measurement of body impedance according to claim 3, wherein said cold terminals of said first and said second set of electrodes are electrically connected together.

5. The device for the measurement of body impedance according to claim 4, wherein said hot terminals of said first and said second set of electrodes are electrically connected together.

6. The device for the measurement of body impedance according to claim 1, characterized in that said sinewave oscillator comprises a low distortion, amplitude controlled oscillator.

7. The device for the measurement of body impedance according to claim 6, wherein said sinewave oscillator further comprises an additional feedback loop for the stabilization of the output signal amplitude.

8. The device for the measurement of body impedance according to claim 7, wherein said feedback loop comprises at least a voltage reference, a differential amplifier and a transconductance operational amplifier.

9. The device for the measurement of body impedance according to claim 8, wherein said differential amplifier measures the difference between the voltage reference and the peak value of the oscillator output to control the transconductance operational amplifier in order to stabilize the output signal amplitude.

10. The device for the measurement of body impedance according to claim 9, wherein said sinewave oscillator output frequency belongs to the range of between about 20 kHz and about 100 kHz.

11. The device for the measurement of body impedance according to claim 1, wherein said differential amplifier comprises four Operational Amplifiers.

12. The device for the measurement of body impedance according to claim 11 wherein each of said operational amplifiers is a model OP467 operational amplifier.

13. The device for the measurement of body impedance according to claim 1, wherein said comparator is a TL3016.

14. The device for the measurement of body impedance according to claim 1, wherein said switch is a MAXIM4564.

15. The device for the measurement of body impedance according to claim 1, wherein the electrodes belonging to said first and second set of electrodes are standard ECG Ag/AgCl electrodes.

16. The device for the measurement of body impedance according to claim 1, wherein the electrodes belonging to said first and second set of electrodes are fabric electrodes.

17. The device for the measurement of body impedance according to claim 1, wherein said electrodes are integrated into wearable measurement systems.

18. The device for the measurement of body impedance according to claim 2, wherein said first set and said second set of electrodes comprise two electrodes, one hot terminal and one cold terminal.

19. The device for the measurement of body impedance according to claim 18, wherein said cold terminals of said first and said second set of electrodes are electrically connected together.

20. The device for the measurement of body impedance according to claim 18, wherein said hot terminals of said first and said second set of electrodes are electrically connected together.

21. The device for the measurement of body impedance according to claim 2 characterized in that said sinewave oscillator comprises a low distortion, amplitude controlled oscillator.

22. The device for the measurement of body impedance according to claim 21, wherein said sinewave oscillator further comprises an additional feedback loop for the stabilization of the output signal amplitude.

23. The device for the measurement of body impedance according to claim 22, wherein said feedback loop comprises at least a voltage reference, a differential amplifier and a transconductance operational amplifier.

24. The device for the measurement of body impedance according to claim 23, wherein said differential amplifier measures the difference between the voltage reference and the peak value of the oscillator output to control the transconductance operational amplifier in order to stabilize the output signal amplitude.

25. The device for the measurement of body impedance according to claim 24, wherein said sinewave oscillator output frequency belongs to the range of between about 20 kHz and about 100 kHz.

26. The device for the measurement of body impedance according to claim 2 wherein said differential amplifier comprises four Operational Amplifiers.

27. The device for the measurement of body impedance according to claim 26 wherein each of said operational amplifiers is a model OP467 operational amplifier.

28. The device for the measurement of body impedance according to claim 2 wherein said comparator is a TL3016.

29. The device for the measurement of body impedance according to claim 2 wherein said switch is a MAXIM4564.

30. The device for the measurement of body impedance according to claim 2 wherein the electrodes belonging to said first and second set of electrodes are standard ECG Ag/AgCl electrodes.

31. The device for the measurement of body impedance according to claim 2 wherein the electrodes belonging to said first and second set of electrodes are fabric electrodes.

32. The device for the measurement of body impedance according to claim 2 wherein said electrodes are integrated into wearable measurement systems.

* * * * *